United States Patent [19]

Reisdorff et al.

[11] 4,097,669
[45] Jun. 27, 1978

[54] 2-SUBSTITUTED-5-TRIFLUOROMETHYL-1,3,4-THIADIAZOLES

[75] Inventors: Josef Helmut Reisdorff, Wuppertal; Wilhelm Brandes, Cologne; Hans Scheinpflug; Bernhard Homeyer, both of Leverkusen; Peter Roessler, Bensberg, all of Germany

[73] Assignee: Bayer Aktiengesellschaft, Leverkusen, Germany

[21] Appl. No.: 705,375

[22] Filed: Jul. 14, 1976

[30] Foreign Application Priority Data

Jul. 26, 1975 Germany ............... 2533604

[51] Int. Cl.² ........................... C07D 285/12
[52] U.S. Cl. ......................... 542/413; 71/90; 260/288 CE; 260/294.8 D; 260/302 H; 260/302 SD; 260/306.7 R; 260/306.8 D; 424/248.51; 424/250; 424/251; 424/258; 424/263; 424/270; 544/134; 544/316; 544/367
[58] Field of Search .............. 260/302 SD; 542/413

[56] References Cited

U.S. PATENT DOCUMENTS 3,562,284  2/1971  Newman et al. ............ 260/302 SD

FOREIGN PATENT DOCUMENTS 1,817,069  6/1970  Germany ................. 260/302 SD

*Primary Examiner*—R. Gallagher
*Attorney, Agent, or Firm*—Burgess, Dinklage & Sprung

[57] ABSTRACT

2-Substituted-5-trifluoromethyl-1,3,4-thiadiazoles of the formula

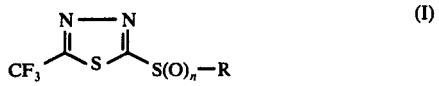

in which
R is substituted alkyl, phenyl monosubstituted in the o- or m- position, polysubstituted phenyl, substituted phenylalkyl, phenylalkenyl, substituted phenylalkenyl, an optionally substituted 5-membered or 6-membered heterocyclic radical with 1 to 4 hetero-atoms selected from N and S atoms, optionally substituted benzimidazolyl or benzthiazolyl, optionally substituted naphthyl, quinolyl, cyano or one of the groups

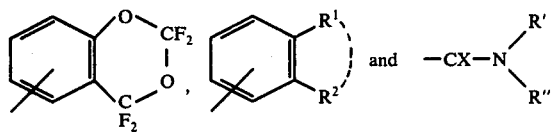

wherein
$R^1$ and $R^2$ conjointly are a trimethylene, tetramethylene or pentamethylene group,
X is oxygen or sulfur,
$R'$ and $R''$ each independently is alkyl or, together with the nitrogen atom and optionally further hetero-atoms selected from O and N atoms, form an optionally substituted 6-membered or 7-membered ring, and
n is 0, 1 or 2, which possess fungicidal, bactericidal, arthropodicidal and insecticidal properties.

8 Claims, No Drawings

2-SUBSTITUTED-5-TRIFLUOROMETHYL-1,3,4-THIADIAZOLES

The present invention relates to and has for its objects the provision of particular new 2-substituted -5-trifluoromethyl-1,3,4-thiadiazoles which possess fungicidal, bactericidal, arthtopodicidal and insecticidal properties, active compositions in the form of mixtures of such compounds with solid and liquid dispersible carrier vehicles, and methods for producing such compounds and for using such compounds in a new way especially for combating pests, e.g. fungi, bacteria, arthropods and insects, with other and further objects becoming apparent from a study of the within specification and accompanying examples.

It has been disclosed in U.S. Pat. No. 3,562,284 that some 2-substituted thio-5-trifluoromethyl-1,3,4-thiadiazoles possess fungicidal properties. However, their activity is not always entirely satisfactory, especially when low amounts and low concentrations are used. These 1,3,4-thiadiazoles are not insecticidally active.

The present invention provides, as new compounds, the 2-substituted 5-trifluoromethyl-1,3,4-thiadiazoles of the general formula

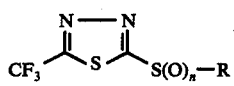

in which

R is substituted alkyl, phenyl monosubstituted in the o- or m- position, polysubstituted phenyl, substituted phenylalkyl, phenylalkenyl, substituted phenylalkenyl, an optionally substituted 5-membered or 6-membered heterocyclic radical with 1 to 4 hetero-atoms selected from N and S atoms, optionally substituted benzimidazolyl or benzthiazolyl, optionally substituted naphthyl, quinolyl, cyano or one of the groups

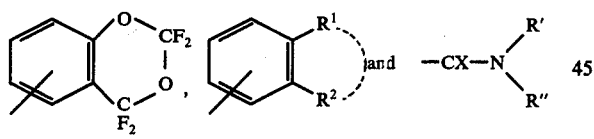

wherein
R$^1$ and R$^2$ conjointly are a trimethylene, tetramethylene or pentamethylene group,
X is oxygen or sulfur,
R' and R" each independently is alkyl or, together with the nitrogen atom and optionally further hetero-atoms selected from O and N atoms, form an optionally substituted 6-membered or 7-membered ring, and
n is 0, 1 or 2,
which possess fungicidal, bactericidal, arthropodicidal and insecticidal properties.

Preferably, R is straight-chain or branched monosubstituted or polysubstituted alkyl with 1 to 6 carbon atoms, with preferred possible substituents being halogen (especially fluorine, chlorine or bromine), cyano, isothiocyano, phenyl, carboxyl, alkylcarbonyl with 1 or 2 carbon atoms in the alkyl moiety, and phenylcarbonyl optionally substituted by halogen or C$_1$-C$_4$ alkyl; or is phenylalkenyl with 2 to 4 carbon atoms in the alkenyl moiety; or is phenyl monosubstituted in the ortho-position or meta-position, polysubstituted phenyl wherein the substituents are identical or different, or monosubstituted or polysubstituted phenylalkyl with, in particular, 1 or 2 carbon atoms in the alkyl part, preferred possible substituents of phenyl in each case independently being alkyl with 1 to 4 carbon atoms, halogenoalkyl, halogenoalkylthio and halogenalkylsulfonyl, each with 1 or 2 carbon atoms and 2 to 5 halogen atoms (especially fluorine), alkoxy, alkylcarbonyl and alkoxycarbonyl, each with 1 to 4 carbon atoms in the alkyl moiety, hydroxyl, carboxyl, nitro, cyano and thiocyano. Other preferred meanings of R are the following 5-membered and 6-membered heterocyclic structures; imidazole optionally substituted in the 1- and/or 4- and/or 5- position with alkyl with 1 or 2 carbon atoms, halogen or nitro; 1,2,4thiadiazole optionally substituted in the 2-position with alkyl with 1 to 4 carbon atoms, amino, alkylcarbonyl, alkylamino and dialkylamino, as well as dialkylaminomethyleneimino and N,N'-dialkylurea, in each case with 1 or 2 carbon atoms in each alkyl moiety, phenyl, chlorophenyl, alkylthio and alkylsulfonyl in each case with 1 or 2 carbon atoms in the alkyl moiety, halogenoalkyl with 1 or 2 carbon atoms and 2 to 5 halogen atoms, and nitro, tetrazole optionally substituted by alkyl with 1 to 2 carbon atoms; thiophene optionally substituted by nitro or halogen; pyridine, pyridine-N-oxide and pyrimidine optionally substituted by alkyl with 1 to 2 carbon atoms or halogen; and thiazoline, tetrahydropyrimidine or tetrahydrothiazine optionally substituted by methyl. Alternatively, R preferably is benzimidazolyl and benzthiazolyl, optionally substituted in the benzene ring by halogen, especially chlorine, or alkoxy with 1 to 2 carbon atoms, or a grouping

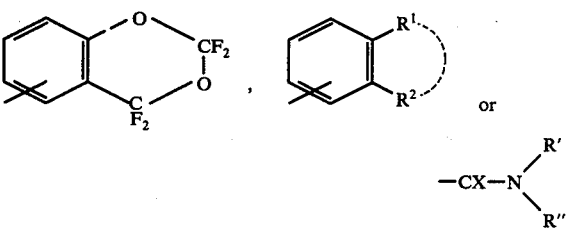

wherein
R$^1$ and R$^2$ conjointly are a trimethylene or tetramethylene group;
X is oxygen or sulfur and
R' and R" each independently is alkyl with 1 or 2 carbon atoms, or form, with the N atom, a perhydrazepine, morpholine- or piperazone-N-hydroxyether ring. Furthermore, R may also preferably be naphthyl optionally substituted by nitro, halogen or alkyl with 1 or 2 carbon atoms, qinolinyl, the quinoline-N-oxide radical and cyano.

Surprisingly, the 2-substituted 5-trifluoromethyl-1,3,4-thiadiazoles according to the invention exhibit a substantially greater fungicidal and insecticidal action, especially a soil-insecticidal and development-inhibiting action, than the 2-substituted thio-5-trifluoromethyl-1,3,4-thiadiazoles known from the state of the art which are chemically the nearest compounds. The compounds according to the invention thus represent an enrichment of the art.

The present invention also provides a process for the preparation of a 2-substituted 5-trifluoromethyl-1,3,4-thiadiazole of the general formula (I) in which
(a) a 2-halogeno-5-trifluoromethyl-1,3,4-thiadiazole of the general formula

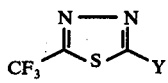
(II), in which
Y represents chlorine or bromine, is reacted with a mercaptan of the general formula

RS — H     (III), in which
R has the above-mentioned meaning, if appropriate in the presence of a solvent and of an acid-binding agent and, if required, the resultant 2-substituted 5-trifluoromethyl-1,3,4-thiadiazole of the general formula

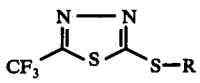
(IV)

in which
R has the above-mentioned meaning, is reacted with an oxidizing agent whereby, depending on the oxidizing agent used, a compound of the formula (I) with $n = 1$ or $n = 2$ is obtained, or
(b) 2-mercapto-5-trifluoromethyl-1,3,4thiadiazole of the formula

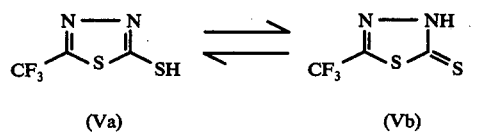
(Va)                (Vb)
(V)

is reacted with a compound of the general formula

Z — R     (VI)

in which
R has the above-mentioned meaning and
Z represents chlorine, bromine, iodine, methanesulfonyloxy or toluenesulfonyloxy, if appropriate in the presence of a solvent and of an acid-binding agent and, if required, the resultant 2-substituted thio-5-trifluoromethyl-1,3,4-thiadiazole of the formula (IV) is reacted with an oxidizing agent whereby, depending on the oxidizing agent, a compound of the formula (I) with $n = 1$ or $n = 2$ is obtained, or
(c) in the case of the preparation of a sulfonyl compound wherein $n = 2$ in the formula (I), a 2-halogeno-5-trifluoromethyl-1,3,4-thiadiazole of the general formula (II) is reacted in the presence of a solvent with a sulfinic acid of the general formula

R—SO$_2$H     (VII), in which
R has the above-mentioned meaning, the sulfinic acid being used as such, in the presence of an inorganic or organic base, or in the form of a corresponding sulfinate.

If 2-bromo-5-trifluoromethyl-1,3,4-thiadiazole and 2-mercaptobenzoic acid are used as starting materials in process variant (a), the course of the reaction can be represented by the following equation:

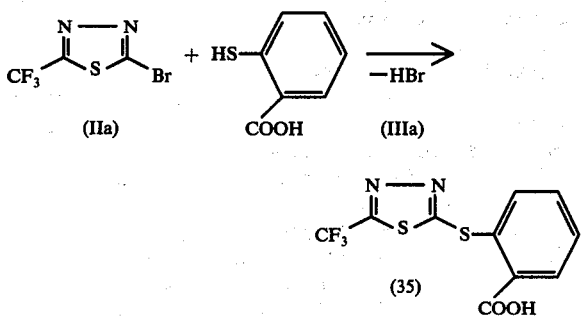

If 2-chloro-5-trifluoromethyl-1,3,4-thiadiazole and 2-mercaptopyrimidine are used as starting materials in process variant (a) and chlorine is used as the oxidizing agent, the course of the reaction can be represented by the following equation:

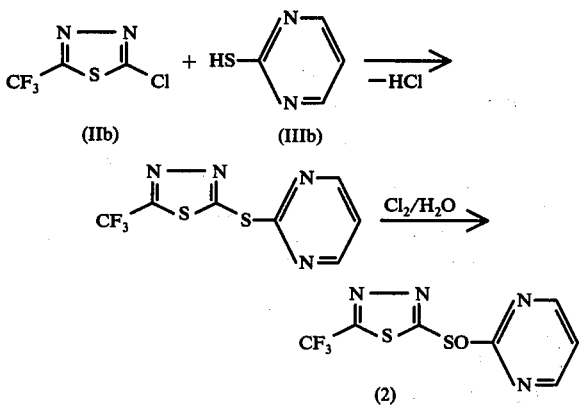

If 2-bromo-5-trifluoromethyl-1,3,4-thiadiazole and 3,5-dimethylthiophenol are used as starting materials in process variant (a) and hydrogen peroxide is used as the oxidizing agent, the course of the reaction can be represented by the following equation:

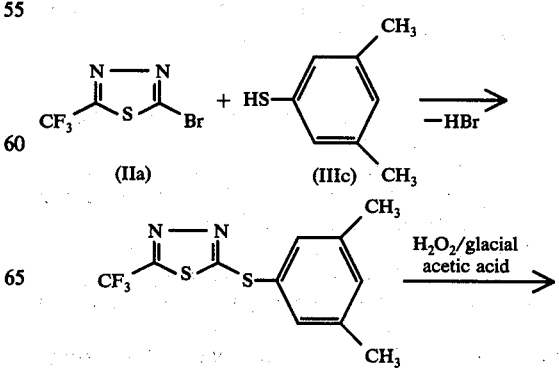

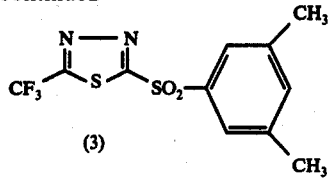

(3)

If 2-mercapto-5-trifluoromethyl-1,3,4-thiadiazole and 2-bromo-5-nitro-thiophene are used as starting materials in process variant (b), the course of the reaction can be represented by the following equation:

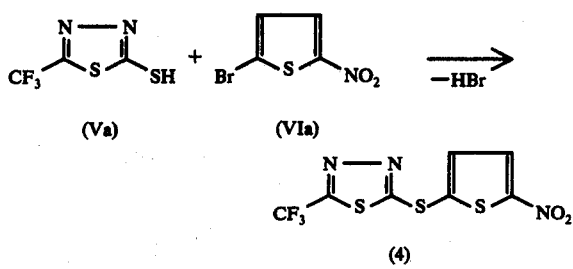

If 2-bromo-5-trifluoromethyl-1,3,4-thiadiazole and naphthalene-2-sulfinic acid, in the presence of sodium hydroxide, are used as starting materials in process variant (c), the course of the reaction can be represented by the following equation:

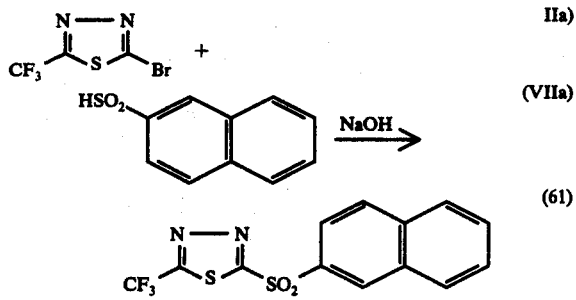

The 2-halogeno-5-trifluoromethyl-1,3,4-thiadiazole of the formula (II) used as the starting material for process variant (a) is already known (see German Offenlegungsschrift (German Published Specification) 2,162,575 and J. Het. Chem. 11, 343–45 (1974)). It is obtained analogously to a method described by Kanaoka (see Pharmaceutical Bulletin 5, 385–389 (1957)) by diazotization of the corresponding 2-aminothiadiazole (for its preparation, see J. Het. Chem. 3, 336–37 (1966)). Surprisingly, it has been found that the reaction described there (Sandmeyer reaction) takes place spontaneously, in high yields, even at temperatures of −5° to +15° C and without the customary addition of copper salts.

Mercaptans which can be used according to the invention are known from Houben-Weyl, volume 9, pages 7–48 (1955) and U.S. Pat. No. 3,798,229; they can, in any case, easily be prepared in accordance with the processes described there. Thus, for example, the aromatic mercaptans are obtained by reaction of the corresponding sulfochlorides with zinc and sulfuric acid (see also the preparative examples herein). To prepare the aliphatic and araliphatic mercaptans, for example, the corresponding bromides are heated with thiourea in ethanol under reflux, and the isothiuronium salts produced are decomposed with aqueous alkali metal hydroxide solution; the mercaptans can then be isolated by customary methods. The following may be mentioned as examples of mercaptans of the formula (III) which can be used according to the invention: 4-mercapto-valeric acid ethyl ester, triphenylmethylmercaptan, 2-chloro-ethylmercaptan, 3-phenyl-allylmercaptan, p-methylphenacylmercaptan, 2,6-dichloro-phenylmercaptan, 2-mercaptoquinoline-N-oxide, 4-chloro-3-methyl-phenylmercaptan, 1,4-bis-mercaptomethylbenzene, ethylenediamine-bis-dithiocarbamate, 4-nitro-benzylmercaptan, pentafluoro-phenylmercaptan, 2-ethoxyphenylmercaptan, 2-isopropylthio-5-mercapto-1,3,4-thiadiazole, 4-trifluoromethoxy-benzylmercaptan, 5-chloro-2-mercapto-naphthalene and 4-chloro-2-mercapto-pyridine-N-oxide.

The 2-mercapto-5-trifluoromethyl-1,3,4-thiadiazole of the formula (V) used as the starting material for process variant (b) is already known (see German Offenlegungsschrift (German Published Specification) 2,162,575). It is obtained by reaction of 2-bromo-5-trifluoromethyl-1,3,4-thiadiazole of the formula (II) with thiourea in boiling ethanol, followed by treatment with sodium hydroxide solution.

The compounds of the formula (VI) which can be used according to the invention are compounds generally known in organic chemistry, and can be prepared in accordance with simple known methods. The following may be mentioned as examples: 2,4-dinitrofluorobenzene, 4-chlorophenyl-trifluoromethylsulfone, 2-iodo-1-methyl-5-nitroimidazole, 1-(2-chloroethyl)-2-methyl-5-nitroimidazole, 2-bromo-5-nitro-1,3,4-thiadiazole, 5-chloro-3-methylmercapto-1,2,4-thiadiazole, N,N-dimethylcarbamoyl chloride, 4-nitrophenethyl bromide, chloromethylisothiocyanate, 2-bromoacetone, chloroacetonitrile, 2,4,5-trichlorothiazole, 1,1,1-trifluoro-2-methanesulfonyloxyethane, 4-chloro-benzyl chloride, 1,3-bis-toluenesulfonyloxypropane, 3,4,5-trichloronitrobenzene and 2-chloromethylpyridine.

The sulfinic acids and sulfinates which can be used according to the invention are compounds generally known in organic chemistry, and can be prepared in accordance with simple, known methods, for example by reduction of the corresponding sulfochlorides with alkali metal sulfites in water, in which case the more stable salts of the sulfinic acids can be employed directly, without isolation, for the further reaction (see Houben-Weyl, Methoden der organischen Chemie (Methods of Organic Chemistry), volume 9, 285–343 (1955), Georg Thieme Verlag Stuttgart).

The following may be mentioned as examples: nonafluorobutanesulfinate, 3,4-dimethylbenzylsulfinate, pyridine-3-sulfinate, thiophene-3-sulfinate 3-bromobenzenesulfinate, 3,4,5-trichlorbenzenesulfinate, 3-bromo-4-nitrobenzenesulfinate, 2-fluorobenzenesulfinate, 6-chloro-naphthalene-2-sulfinate, 2,3-dichlorobenzenesulfinate bromomethylsulfinate, benzothiazole-2-sulfinate, 1,4-butane-disulfinate, 2-methylbenzenesulfinate, 3-methyl-4-trifluoromethylthiobenzenesulfinate, 2-(4-chlorophenol)-vinylsulfinate, 4-methylnaphthalene-2-sulfinate and 2,4-dimethoxybenzenesul.

Preferred diluents for the reaction according to the invention, in accordance with process variant (a), are water and inert organic solvents, especially ketones, such as diethyl ketone, and, more especially, acetone and methyl ethyl ketone; nitriles, such as propionitrile and especially acetonitrile; alcohols, such as ethanol or isopropanol; ethers, such as tetrahydrofuran or dioxane; hydrocarbons, such as ligroin, petroleum ether, benzene, toluene and xylene; chlorinated hydrocarbons, such as chloroform, carbon tetrachloride and methylene chloride; and formamides, such as, in particular, dimethylformamide.

The reaction according to process variant (a) is generally carried out in the presence of an acid-binding agent. It is possible to add any of the inorganic or organic acid acceptors usually employable, such as alkali metal carbonates, for example sodium carbonate, potassium carbonate and sodium bicarbonate; lower tertiary alkylamines, cycloalkylamines or aralkylamines, for example triethylamine, dimethylbenzyl- and cyclohexylamine; bases such as pyridine and diazabicyclooctane; alkali metal alcoholates, for example sodium methylate and potassium ethylate; or alkali metal hydroxides, for example sodium hydroxide and potassium hydroxide.

In process variant (a), the reaction temperatures can be varied within a fairly wide range. In general, the reaction is carried out at from 0° to 120°, preferably at 20° to 100° C. In the presence of a solvent, the reaction is suitably carried out at the boiling point of the particular solvent.

In carrying out process variant (a) preferably about 1 mole of the mercaptan of the formula (III) and about 1 mole of acid-binding agent are employed per mole of the compound of the formula (II).

To isolate the compounds of the formula (I), either the reaction mixture is poured onto ice water, the batch filtered and the retained precipitate washed, if appropriate, and dried, or the reaction mixture is washed with water and the organic phase is separated off, dried and freed from the solvent, or the salt (by-product) which has precipitated is filtered off and the reaction product is isolated from the filtrate. The reaction products can, if desired, be purified by recrystallization or distillation.

In accordance with process variant (a), the compounds of the formula (IV), thus obtained, can then be oxidized. All inorganic and organic oxidizing agents which can usually be employed may be considered, such as chlorine in water, per-acids, for example m-chloroperbenzoic acid, hydrogen peroxide in glacial acetic acid or in methanol, potassium permanganate and chromic acid.

The reaction temperatures for the oxidation according to process variant (a) can be varied within a fairly wide range. In general, the reaction is carried out at between $-30°$ and $+100°$ C, preferably at $-10°$ to 80° C.

In carrying out the oxidation according to process variant (a), 1 to 4 moles of oxidizing agent are generally employed per mole of the compound of the formula (IV). When using 1 mole of oxidizing agent, such as m-chloroperbenzoic acid in methylene chloride, or hydrogen peroxide in acetic anhydride, at temperatures between $-10°$ and $+10°$ C, the compounds of the formula (I) wherein $n = 1$ are produced preferentially. If an excess of oxidizing agent and higher temperatures (say 10° to 80° C) are used, the compounds of the formula (I) wherein $n = 2$ are produced preferentially.

To isolate the oxidation products, either the reaction mixture is poured onto ice water, the batch filtered and the retained precipitate washed, if appropriate, and dried, or the reaction solution is brought to pH 7 to 8 and extracted with an organic solvent, the extracted phase is dried and the solvent is distilled off. In both cases the reaction products can be purified by recrystallization or column chromatography.

Preferred diluents for the reaction according to the invention, in accordance with process variant (b), include water and polar organic solvents, especially nitriles, such as acetonitrile; sulfoxides, such as dimethylsulfoxide; formamides, such as dimethylformamide; ketones, such as acetone; ethers, such as diethyl ether and tetrahydrofuran; and chlorohydrocarbons, such as methylene chloride and chloroform.

The reaction according to process variant (b) is carried out in the presence of an acid-binding agent, which is preferably selected from the inorganic or organic acid-binding agents already mentioned for process variant (a).

The reaction temperatures for process (b) correspond to those of process (a).

In carrying out the process variant (b) preferably about 1 mole of the halide of the formula (VI) and about 1 mole of acid-binding agent are employed per mole of the compound of the formula (V).

The isolation of the compounds of the formula (I) is generally carried out in the same manner as that already described for process variant (a).

The conditions (oxidizing agent, temperature range and isolation) of the optional oxidation in process variant (b) are the same as those already described for process variant (a).

Preferred diluents for the reaction according to process variant (c) are those already mentioned for process variant (a).

The reaction according to process variant (c) is carried out in the presence of a base. It is possible to use all customary inorganic and organic bases, such as alkali metal hydroxides, for example sodium hydroxide and potassium hydroxide, or such as lower tertiary alkylamines, for example triethylamine.

The reaction temperatures for process variant (c) correspond to those of process (a).

In carrying out process variant (c), about 1 mole of the sulfinic acid of the formula (VII) is generally employed per mole of the compound of the formula (II).

To isolate the compounds of the formula (I), the reaction mixture is poured onto ice water and the batch is filtered. The retained precipitate is dried and purified by recrystallization.

The active compounds according to the invention exhibit a powerful fungitoxic and bacteriotoxic action. They do not damage crop plants in the concentrations required for combating fungi and bacteria. For these reasons, they are suitable for use as plant protection agents for combating fungi and bacteria. Fungitoxic agents are employed in plant protection for combating Archimycetes, Phycomycetes, Ascomycetes, Basidiomycetes and *Fungi Imperfecti*.

The active compounds according to the invention have a broad spectrum of action and can be employed against parasitic fungi and bacteria which attack above-ground parts of plants or attack the plants through the soil, and also against seed-borne pathogens. They exhibit a particularly good activity against, for example, species of Pythium, species of Phytophthora, species of Fusarium, species of Fusicladium, *Verticillium alboatrum*, species of Botrytis, *Cochliobolus miyabeanus* and *Phialophora cinerescens*. The compounds according to the invention are also active against cereal diseases, such as, for example, against bunt of wheat.

As plant protection agents, the active compounds according to the invention can be used for the treatment of seed and for the treatment of above-ground parts of plants.

The active compounds according to the invention furthermore exhibit a good insecticidal action, especially a powerful soil-insecticidal action. They furthermore exhibit a good development-inhibiting action on insects or spider mites, by which action a development to the chrysalis or the sexually mature imagos is prevented. This action starts during the shedding of skin which is only typical of arthropods. In some cases the action ceases through several stages of development and only comes into play during the pupation or slipping sequences. The active compounds can therefore be used with good success for combating sucking and biting insects and Diptera.

To the sucking insects there belong in the main aphids such as the green peach aphid (*Myzus persicae*) and the bean aphid (*Doralis fabae*); scales, such as *Aspidiotus hederae, Lecanium hesperidum* and *Pseudococcus maritimus;* Thysanoptera, such as Hercinothrips femoralis; and bugs, such as the beet bug (*Piesma quadrata*) and the bed bug (*Cimex lectularius*).

To the biting insects there belong in the main butterfly and moth caterpillars, such as *Plutella maculipennis* and *Lymantria dispar;* beetles, such as the granary weevil (*Sitophilus granarius*) and the Colorado beetle (*Leptinotarsa decemlineata*), and also species living in the soil, such as the wireworms (Agriotes spec.) and larvae of the cockchafer (*Melolontha melolontha*); cockroaches, such as the German cockroach (*Blattella germanica*); Orthoptera, such as the house cricket (*Gryllus domesticus*); termites, such as Reticulitermes; Hymenoptera, such as ants.

The Diptera comprise essentially the flies, such as the vinegar fly (*Drosophila melanogaster*), the Mediterranean fruit fly (*Ceratitis capitata*), the house fly (*Musca domestica*) and mosquitoes, such as the yellow fever mosquito (*Aedes aegypti*).

The active compounds according to the invention furthermore show herbicidal and microbistatic actions when used in appropriate amounts and concentrations.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chlorethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.) and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier verhicles and/or with other known compatible active agents, especially plant treating agents, such as other fungicides, bactericides, arthropodicides and herbicides, or nematocides, rodenticides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0001-10%, preferably 0.01-1%, by weight of the mixture. Thus, the present invention contemplates overall compositions which comprise mixture of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95% and preferably 0.01-95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50-100 microns, or even less, i.e. mist form, for examples by airplane crop spraying techniques. Only up to at most about a few liters/hectare are needed, and often amounts only up to about 15 to 1000 g/hectare, preferably 40 to 600 g/hectare, are sufficent. In this process it is possible to use highly concentrated liquid compositions with said liquid carrier vehicles containing from about 20 to about 95% by weight of the active compound or even the 100% active substance alone, e.g. about 20–100% by weight of the active compound.

In the treatment of seed, amounts of active compound of 0.001 to 50 g, preferably 0.01 to 10 g, per kg of seed are generally employed.

Furthermore, the present invention contemplates methods of selectively killing, combating or controlling pests, e.g. nematodes, insects, acarids and fungi, and more particularly methods of combating nematodes, which comprises applying to at least one of correspondingly (a) such nematodes, (b) such insects, (c) such acarids, (d) such fungi, and (e) the corresponding habitat thereof, i.e. the locus to be protected, e.g. to a growing crop, to an area where a crop is to be grown or to a domestic animal, a correspondingly combative or toxic amount, i.e. a nematocidally, insecticidally, acaricidally or fungicidally effective amount, of the particular active compound of the invention alone or together with a carrier verhicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Fusicladium test (apple)/(protective)

Solvent: 4.7 parts by weight of acetone

Emulsifier: 0.3 part by weight of alkylaryl polyglycol ether

Water: 95 parts by weight

The amount of active compound required for the desired concentration of the active compound in the spray liquid was mixed with the stated amount of solvent, and the concentrate was diluted with the stated amount of water which contained the stated additions.

Young apple seedlings in the 4 – 6 leaf stage were sprayed with the spray liquid until dripping wet. The plants remained in a greenhouse for 24 hours at 20° C and at a relative atmospheric humidity of 70%. They were then inoculated with an aqueous conidium suspension of the apple scab causative organism (*Fusicladium dendriticum*) and incubated for 18 hours in a humidity chamber at 18°–20° C and at a relative atmospheric humidity of 100%.

The plants were then brought into a greenhouse for 14 days.

15 days after inoculation, the infection of the seedlings was determined. The assessment data were converted to per cent infection. 0% means no infection; 100% means that the plants were totally infected.

The active compounds, the concentrations of the active compounds and the results can be seen from the following table:

Table 1

*Fusicladium* test (apple)/protective

| Active compound | Infection in % at an active compound concentration of 0.00062% |
|---|---|
| 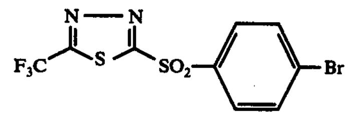  (known) (A) | 16 |
| 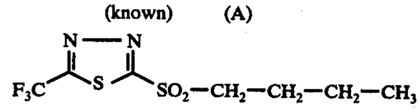  (known) (B) | 66 |
| 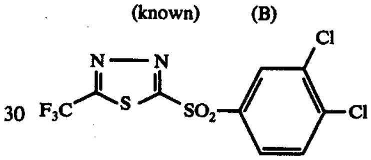  (55) | 0 |
|  (57) | 0 |
| 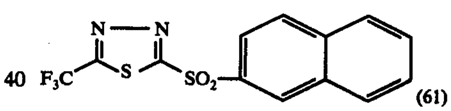  (61) | 0 |
| 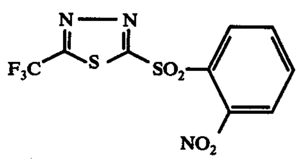  (63) | 6 |
| 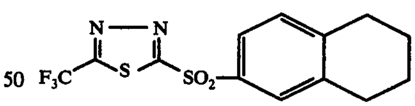  (64) | 2 |
|  (3) | 1 |
|  (67) | 7 |
|  (69) | 1 |

Table 1-continued

*Fusicladium* test (apple)/protective

| Active compound | Infection in % at an active compound concentration of 0.00062% |
|---|---|
| (70) F₃C-[thiadiazole]-SO₂-[2,5-dichlorophenyl] | 0 |
| (71) F₃C-[thiadiazole]-SO₂-CH=CH-[phenyl] | 0 |
| (53) F₃C-[thiadiazole]-SO₂-[2,4-dichlorophenyl] | 2 |

EXAMPLE 2

Phytophthora test (tomatoes)/protective
Solvent: 4.7 parts by weight of acetone
Emulsifier: 0.3 part by weight of alkylaryl polyglycol ether
Water: 95 parts by weight The amount of the active compound required for the desired concentration of the active compound in the spray liquid was mixed with the stated amount of solvent and the concentrate was diluted with the stated amount of water which contained the stated additions.

Young tomato plants with 2 to 4 foliage leaves were sprayed with the spray liquid until dripping wet. The plants remained in a greenhouse for 24 hours at 20° C and at a relative atmospheric humidity of 70%. The tomato plants were then inoculated with an aqueous spore suspension of *Phytophthora infestans*. The plants were brought into a moist chamber with an atmospheric humidity of 100% and a temperature of 18°–20° C.

After 5 days the infection of the tomato plants was determined. The assessment data were converted to per cent infection: 0% means no infection; 100% means that the plants were totally infected.

The active compound, the concentrations of the active compound and the results can be seen from the following table:

Table 2

*Phytophthora* test (tomatoes)/protective

| Active compound | Infection in % at an active compound concentration of 0.00156 |
|---|---|
| (A) (known) F₃C-[thiadiazole]-SO₂-[4-bromophenyl] | 35 |
| (B) (known) F₃C-[thiadiazole]-SO₂-CH₂-CH₂-CH₂-CH₃ | 91 |
| (57) F₃C-[thiadiazole]-SO₂-[chlorophenyl] | 27 |
| (61) F₃C-[thiadiazole]-SO₂-[naphthyl] | 16 |
| (3) F₃C-[thiadiazole]-SO₂-[dimethylphenyl] | 22 |
| (69) F₃C-[thiadiazole]-SO₂-[CF₃,Cl-phenyl] | 30 |
| (70) F₃C-[thiadiazole]-SO₂-[2,5-dichlorophenyl] | 10 |
| (71) F₃C-[thiadiazole]-SO₂-CH=CH-[phenyl] | 17 |
| (24) F₃C-[thiadiazole]-S-[thiadiazole]-SCH₃ | 14 |
| (53) F₃C-[thiadiazole]-SO₂-[2,4-dichlorophenyl] | 4 |

EXAMPLE 3

Mycelium growth test
Nutrient medium used:
  20 parts by weight of agar-agar
  200 parts by weight of potato decoction
  5 parts by weight of malt
  15 parts by weight of dextrose
  5 parts by weight of peptone
  2 parts by weight of disodium hydrogen phosphate
  0.3 part by weight of calcium nitrate
Composition of the solvent mixture:
  0.19 part by weight of DMF or acetone
  0.01 part by weight of emulsifier (alkylaryl polyglycol ether)

1.80 parts by weight of water
Ratio of solvent mixture to nutrient medium:
2 parts by weight of solvent mixture
100 parts by weight of agar nutrient medium The amount of active compound required for the desired active compound concentration in the nutrient medium was mixed with the stated amount of solvent mixture. The concentrate was thoroughly mixed, in the stated proportion, with the liquid nutrient medium (which had been cooled to 42° C) and was then poured into Petri dishes of 9 cm diameter. Control plates to which the preparation had not been added were also set up.

When the nutrient medium had cooled and solidified, the plates were inoculated with the species of fungi stated in the table and incubated at about 21° C.

Evaluation was carried out after 4–10 days, dependent upon the speed of growth of the fungi. When evaluation was carried out the radial growth of the mycelium on the treated nutrient media was compared with the growth on the control nutrient medium. In the evaluation of the fungus growth, the following characteristic values were used:

1 no fungus growth
up to 3 very strong inhibition of growth
up to 5 medium inhibition of growth
up to 7 slight inhibition of growth
9 growth equal to that of untreated control.

The active compounds, the active compound concentrations and the results can be seen from the following table:

Table 3

| Active compounds | Active compound concentration = 10 ppm | Fusarium culmorum | Fusarium nivale | Cochliobolus miyabeanus | Botrytis cinerea | Verticillium alboatrum | Phialaphora cinerescen | Phytophthora cactorum |
|---|---|---|---|---|---|---|---|---|
| 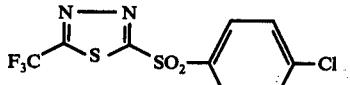 (known) | — | 5 | 5 | 5 | 9 | 9 | — | — |
| 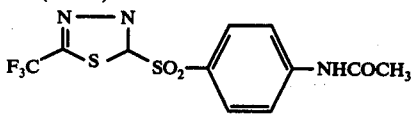 (known) | (C) 5 | 5 | 5 | 9 | 3 | 5 | 2 | |
| 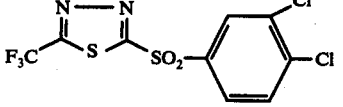 | (D) (55) | 1 | 1 | 2 | 1 | 1 | 5 | — |
| 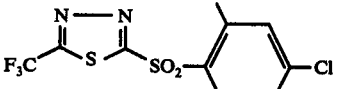 | (56) | 1 | 1 | 3 | — | 3 | — | 5 |
| 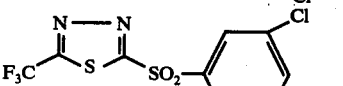 | (57) | 1 | 1 | 2 | 1 | 1 | 1 | 1 |
| 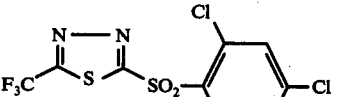 | (58) | 3 | 3 | 2 | 3 | 1 | 5 | 1 |
| 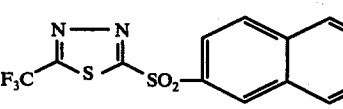 | (61) | 2 | 2 | 1 | 2 | 5 | 1 | 3 |
| 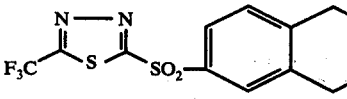 | (64) | 1 | 1 | 5 | 3 | 5 | 5 | — |
| 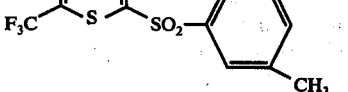 | (3) | 1 | 1 | 3 | 5 | 5 | 5 | 3 |
| 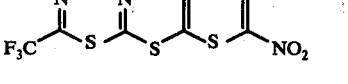 | (4) | 1 | 1 | 1 | 3 | 5 | 5 | 1 |

Table 3-continued

| Active compounds | Mycelium growth test Active compound concentration = 10 ppm | Fusarium culmorum | Fusarium nivale | Cochliobolus miyabeanus | Botrytis cinerea | Verticillium alboatrum | Phialaphora cinerescen | Phytophthora cactorum |
|---|---|---|---|---|---|---|---|---|
| [F₃C-thiadiazole-S-S-thiadiazole] | (23) | 1 | 2 | 5 | 1 | 1 | 2 | 1 |
| [F₃C-thiadiazole-S-S-thiadiazole-SO₂-CH₃] | (25) | 1 | 3 | 1 | 1 | 1 | 1 | 1 |
| [F₃C-thiadiazole-S-S-C(=S)-N-morpholine] | (39) | 1 | 1 | 1 | 2 | 3 | 5 | 3 |
| [F₃C-thiadiazole-S-imidazole-diphenyl] | (10) | 1 | 1 | 1 | 1 | 5 | 5 | 1 |
| [F₃C-thiadiazole-S-S-thiadiazole-CF₃] | (41) | 1 | 3 | 1 | 5 | 5 | 5 | 1 |
| [F₃C-thiadiazole-S-S-C=CH-NO₂] | (42) | 1 | 1 | 1 | 1 | 1 | 1 | 1 |
| [F₃C-thiadiazole-S-S-tetrazole-CH₃] | (17) | 1 | 1 | 5 | 2 | 3 | 5 | — |
| [F₃C-thiadiazole-S-S-C(=S)-N(CH₃)₂] | (38) | 1 | 1 | 1 | 5 | 3 | 2 | — |
| [F₃C-thiadiazole-SO₂-dichlorophenyl] | (6) | 1 | 3 | 1 | 5 | — | — | — |
| [F₃C-thiadiazole-SO₂-methylnitrophenyl] | (67) | 1 | 5 | 3 | 5 | — | — | — |
| [F₃C-thiadiazole-SO₂-dichlorophenyl] | (53) | 5 | 5 | 3 | 5 | 1 | 1 | 1 |
| [F₃C-thiadiazole-S-S-C(CH₃)=N-N=CH] | (43) | 1 | 2 | 1 | 3 | 3 | 1 | — |

EXAMPLE 4

Seed dressing test/bunt of wheat (seed-borne mycosis)

To produce a suitable dry dressing, the active compound was extended with a mixture of equal parts by weight of talc and kieselguhr to give a finely powdered mixture with the desired concentration of the active compound.

Wheat seed was contaminated with 5 g of the chlamydospores of *Tilletia caries* per kg of seed. To apply the dressing, the seed was shaken with the dressing in a closed glass flask. The seed, on moist loam under a cover of a layer of muslin and 2 m of moist compost soil, was exposed to optimum germination conditions for the spores for 10 days at 10° C in a refrigerator.

The germination of the spores on the wheat grains, each of which was contaminated with about 100,000 spores, was subsequently determined microscopically. The smaller the number of spores which had germinated, the more effective was the active compound.

The active compounds, the concentrations of the active compounds in the dressing, the amounts of dressing used and the percentage spore germination can be seen from the following table:

Emulsifier: 1 part by weight of alkylaryl polyglycol ether

To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by Table 4

| Seed dressing test/bunt of wheat | | | |
|---|---|---|---|
| | Active compound concentration in the dressing in % by weight | Amount of dressing used in g/kg of seed | Spore germination in % |
| without dressing | — | — | >10 |
| F$_3$C-[N=N/S]-SO$_2$-C$_6$H$_4$-Br (known) (A) | 25 | 1 | 0.5 |
| F$_3$C-[N=N/S]-SO$_2$-CH$_2$-CH$_2$-CH$_2$-CH$_3$ (known) (B) | 25 | 1 | >10 |
| F$_3$C-[N=N/S]-S-[N=N/S]-CF$_3$ (41) | 25 | 1 | 0.05 |
| F$_3$C-[N=N/S]-S-[N=N/S]-NO$_2$ (42) | 25 | 1 | 0.05 |
| F$_3$C-[N=N/S]-S-(pyridine N-oxide) (8) | 25<br>10<br>5 | 1<br>1<br>1 | 0.0<br>0.0<br>0.0 |
| F$_3$C-[N=N/S]-S-[N=N/S]-NHCH$_3$ (11) | 25 | 1 | 0.05 |
| F$_3$C-[N=N/S]-SO$_2$-C$_6$H$_4$-Cl (57) | 25 | 1 | 0.05 |
| F$_3$C-[N=N/S]-SO$_2$-C$_6$H$_4$-CF$_3$ (60) | 25 | 1 | 0.05 |

EXAMPLE 5

Critical concentration test/soil insects
Test insect: Tenebrio molitor larvae in the soil
Solvent: 3 parts by weight of acetone weight of active compound per unit volume of soil, which is quoted hereinafter in ppm (=mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness is 100% if all the test insects had been killed and is 0% if exactly as many test insects were still alive as in the case of the untreated control.

The active compounds, amounts used and results can be seen from the table which follows:

Table 5
Soil insecticides
Tenebrio molitor larvae in the soil

| Active compound | Active compound concentration in ppm | Degree of destruction in % |
|---|---|---|
| 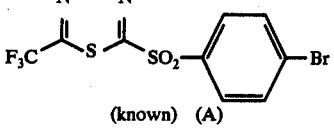 (known) (A) | 10 | 0 |
| 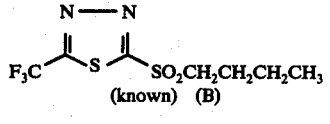 (known) (B) | 10 | 0 |
| 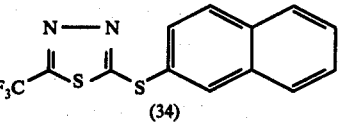 (34) | 10 | 100 |
| 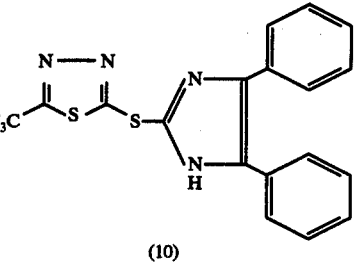 (10) | 10 | 100 |
| 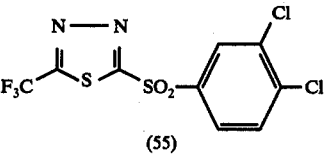 (55) | 10 | 100 |
| 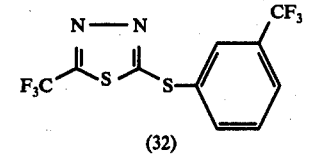 (32) | 10 | 100 |

The Examples 6 and 7 given in the text which follows show the action of the compounds according to the invention in inhibiting the development of arthropods, without it being wished to impose a limitation with regard to the breadth of action of these compounds. During the entire stated development of the test arthropods, the morphological changes, such as half-pupated arthropods, incompletely slipped larvae or caterpillars, defective wings and pupal cuticles in imagos, as well as the mortality, were assessed. The sum of the morphological malformations and of the destruction during development is shown as a percentage of the test arthropods employed.

EXAMPLE 6

Development-inhibiting action/ingestion test

| Test insects | Plutella maculipennis (caterpillars, 4th stage), 20 individuals Phaedon cochleariae (larvae), 20 individuals |
|---|---|
| Feed plants | Cabbage plants (Brssica oleracea) |
| Solvent | 10 parts by weight of acetone |
| Emulsifier | 2.5 parts by weight of alkylaryl polyglycol ether |

To produce a suitable preparaton of active compound, 2 parts by weight of active compound were mixed with the stated amount of solvent and emulsifier and sufficient water to give a 1% strength mixture, which was diluted with water to the desired concentration.

The test insects were fed with leaves of the feed plant, which were provided with a uniform spray coating of the active compound mixture, of the stated concentration, until the imago developed.

For control, the insects were fed with leaves treated only with solvent and emulsifier of the stated concentration. The results can be seen from the table which follows:

Table 6
Development-inhibiting action/ingestion test

| Active compound | Inhibition of development in % at an active compound concentration of 0.01% | |
|---|---|---|
| | Plutella | Phaedon |
| 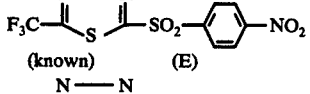 (known) (E) | 0 | 20 |
| 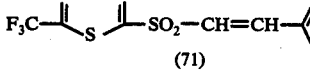 (71) | 100 | 40 |
| 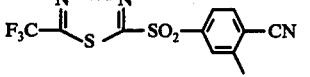 (76) | 100 | 70 |
| 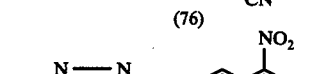 (77) | 100 | 60 |

EXAMPLE 7

Development-inhibiting action/Laphygma test

| Test insects | Laphygma exigua (caterpillars) |
|---|---|
| Feed | 1 cm thick discs, of 3 cm diameter, of ain-dried synthetic feed consisting of shredded bean seeds, yeast, vitamin mixture, powdered leaves, agar and preservative |
| Solvent | 10 parts by weight of acetone |
| Emulsifier | 2.5 parts by weight of alkylaryl polyglycol ether |

To produce a suitable preparation of active compound, 2 parts by weight of active compound were mixed with the stated amount of solvent and emulsifier and sufficient water to give a 1% strength mixture, which was diluted with water to the desired concentration.

Test insects were placed each on a separate feed disc moistened with 1.2 ml of active compound solution of the stated concentration and observed until the imago slipped.

As a control, test insects were placed each on a separate feed disc moistened with 1.2 ml of solvent and emulsifier of the corresponding concentration and observed until the imago slipped. The results can be seen from the table which follows:

Table 7

| | Development-inhibiting action/*Laphygma* test | |
|---|---|---|
| | Inhibition of development in % at an active compound concentration of | |
| Active compound | 0.1% | 0.01% |
| 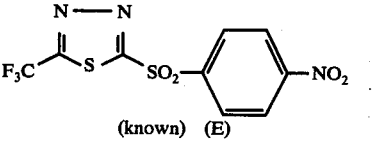 (known) (E) | 40 | 20 |
| 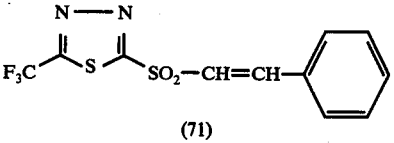 (71) | 100 | 60 |

The process according to the present invention is illustrated by the following preparative Examples:

EXAMPLE 8 (PROCESS VARIANt (A))

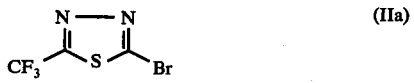 (IIa)

A solution of 69 g (1.0 mole) of sodium nitrite in 150 ml of water was added dropwise over the course of 1.5 hours, while stirring, to a solution, cooled to +5° C, of 84.5 g (0.5 mole) of 2-amino-5-trifluoromethyl-1,3,4-thiadiazole in a mixture of 400 ml of hydrogen bromide (48% strength) and 100 ml of water. Thereafter, the evolution of the nitrous gases and of the nitrogen was completed by stirring at 25° C (1 hour). The product separated out as a dark brown, heavy liquid and was abstracted from the reaction mixture by repeated extraction with a total of 500 ml of methylene chloride. After washing with 2 × 100 ml of water, drying over sodium sulfate and careful distillation of the solvent, the residue was fractionated in vacuo through a short column. 101 g (87% of theory) of 2-bromo-5-trifluoromethyl-1,3,4-thiadiazole of boiling point 55° C/10 mm Hg were obtained.

(b)

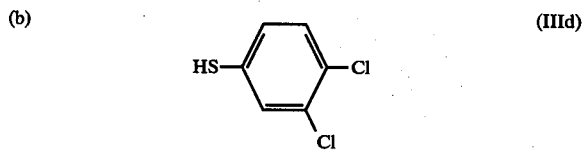 (IIId)

37.5 g (0.15 mole) of 3,4-dichlorobenzenesulfochloride were added dropwise over the course of 30 minutes to a stirred mixture of 400 g of ice and 60 ml of concentrated sulfuric acid at 0° C. Thereafter, 54.5 g (0.84 g atom) of zinc dust were introduced in portions. The mixture was stirred for 1 hour at room temperature and 6 hours under reflux. The thiophenol was steam-distilled, extracted with chloroform and subsequently distilled in vacuo. 13.1 g (47% of theory) of 3,4-dichlorothiophenol of b.p. 114°–115° C/0.08 mm Hg were obtained.

(c)

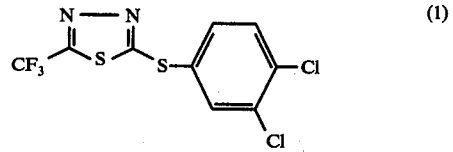 (1)

130.5 g (0.66 mole) of 2-bromo-5-trifluoromethyl-1,3,4-thiadiazole were added dropwise to a solution of 98.1 g (0.66 mole) of 3,4dichloro-thiophenol and 57.6 g (0.66 mole) of triethylamine in 500 ml of ethanol. An exothermic effect was observed and a white precipitate separated out. The mixture was stirred for a further 2 hours under reflux, concentrated to half in vacuo and introduced into 1 liter of ice water. The white precipitate was filtered off, dried over phosphorus pentoxide and recrystallized from about 300 ml of petroleum ether. 147 g (76% of theory) of 2-(3',4'-dichlorophenyl-thio)-5-trifluoromethyl-1,3,4-thiadiazole of melting point 46° C were obtained.

EXAMPLE 9 (PROCESS VARIANT (A) WITH OXIDATION)

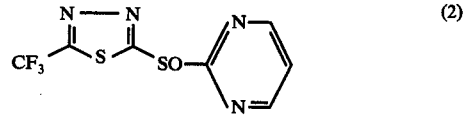 (2)

22.6 g (0.223 mole) of triethylamine, 25 g (0.223 mole) of 2-mercapto-pyrimidine and 52.2 g (0.223 mole) of 2-bromo-5-trifluoromethyl-1,3,4-thiadiazole in 250 ml of tetrahydrofuran were stirred for 3 hours under reflux, concentrated to half in vacuo and introduced into 500 ml of ice water. The precipitate was filtered off, dried and recrystallized from petroleum ether/ethyl acetate (3:1). 44.1 g (75% of theory) of 2-pyrimidyl-(2)-thio-5-trifluoromethyl-1,3,4-thiadiazole of melting point 102° C were obtained. 31.9 g (0.121 mole) thereof were suspended in 30 ml of water. Chlorine was slowly passed in at 0° to 5° C until the mixture was saturated, during which time a precipitate separated out. After 2 hours at 0° C, the mixture was adjusted to pH 8 with potassium carbonate solution and extracted with chloroform, the extract was concentrated and the residue was recrystallized from ethyl acetate. 17.4 g (51% of theory) of 2-pyrimidyl-(2)-thionyl-5-trifluoromethyl-1,3,4thiadiazole of melting point 184° C were obtained.

EXAMPLE 10 (PROCESS VARIANT (A) WITH OXIDATION)

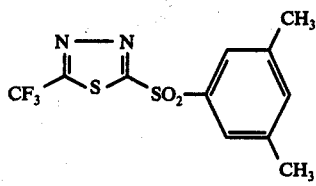 (3)

8.5 g (0.061 mole) of 3,5-dimethylthiophenol, 6.2 g (0.061 mole) of triethylamine and 14.3 g (0.061 mole) of 2-bromo-5-trifluoromethyl-1,3,4-thiadiazole in 150 mole of tetrahydrofuran were stirred for 30 minutes under reflux. The salt (by-product) which had precipitated was filtered off and washed thoroughly with tetrahydrofuran. After distilling off the solvent in vacuo, a colorless oil passed over on distillation. 16.8 g (95% of theory) of 2-(3',5'-dimethylphenylthio)-5-trifluoromethyl-1,3,4-thiadiazole of boiling point 107°–108° C/10.2 mm Hg were obtained. 22.8 g (0.201 mole) of hydrogen peroxide (30% strength) in 100 ml of glacial acetic acid were added thereto and the reaction mixture was stirred for 15 hours at 60° C, and poured onto ice water. The precipitate was filtered off and recrystallized from ethanol. 12.7 g (54% of theory) of 2-(3',5'-dimethylphenyl-sulfonyl)-5-trifluoromethyl-1,3,4-thiadiazole of melting point 110° C were obtained.

EXAMPLE 11 (PROCESS VARIANT (B))

(a) Preparation of the starting material

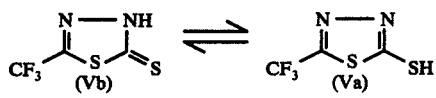

699 g (3 moles) of 2-bromo-5-trifluoromethyl-1,3,4-thiadiazole and 248 g (3.3 moles) of thiourea in a mixture of 600 ml of ethanol and 75 ml of water were heated for 2 hours under reflux. A solution of 223 g of potassium hydroxide in 2 liters of water was rapidly added dropwise to the reaction solution while it was still hot, and the mixture was once more heated under reflux, for 5 minutes. The cooled solution was adjusted to pH 5 with dilute hydrochloric acid and extracted repeatedly with methylene chloride. After drying and concentrating, the residue was recrystallized from a litte petroleum ether. The mother liquor yielded further product. 330 g (59% of theory) of 2-mercapto-5-trifluoromethyl-1,3,4-thiadiazole of melting point 73° C were obtained.

(b)

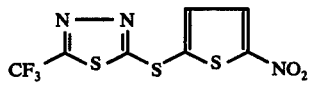 (4)

A mixture of 18.6 g (0.1 mole) of 2-mercapto-5-trifluoromethyl-1,3,4-thiadiazole and 5.6 g (0.1 mole) of powdered potassium hyroxide in 100 ml of absolute dimethylformamide was stirred for 30 minutes. 20.8 g (0.1 mole) of 2-bromo-5-nitro-thiophene were added in a single portion. The mixture was stirred for 3 hours at 50° C, diluted with water and extracted with methylene chloride and after drying the organic phase was evaporated over sodium sulfate. Vacuum distillation gave 24.4 g of crude product of boiling point 160°–163° C/0.3 mm Hg, which was recrystallized from hexane/ethyl acetate (10:1). After further recrystallization ether/petroleum ether (4:3), 17.3 g (55% of theory) of pure 2-(5'-nitro-thiophen-2'-yl-thio)-5-trifluoromethyl-1,3,4-thiadiazole of melting point 57° c were obtained.

EXAMPLE 12 (PROCESS VARIANT (B) WITH OXIDATION)

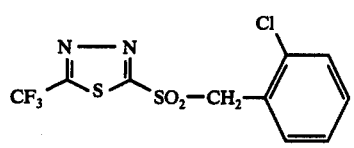 (5)

9.3 g (0.05 mole) of 2-mercapto-5-trifluoromethyl-1,3,4-thiadiazole, 5.1 g (0.05 mole) of triethylamine and 8.1 g (0.05 mole) of o-chlorobenzyl chloride in 80 ml of absolute ethanol were stirred for 2 hours under nitrogen at 50° C and then poured onto ice. The precipitate was filtered off and purified by low temperature crystallization from petroleum ether. 10 g (64% of theory) of 2-(o-chlorobenzylthio)-5-trifluoromethyl-1,3,4-thiadiazole of melting point 36°–37° C were obtained. A solution of 9.8 g (0.048 mole) of m-chloroperbenzoic acid (85% pure) in 85 ml of methylene chloride was added dropwise to 5 g (0.016 mole) of the above compound in 10 ml of methylene chloride. The mixture was stirred for 4.5 hours under reflux and then mixed successively with a solution of 6.4 g of sodium sulfite in a little water, followed by a solution of 2.7 g of sodium carbonate in a little water, and stirred thoroughly for 15 minutes. The organic phase, after concentration and recrystallization from cyclo-hexane/ethyl acetate, gave colorless crystals. 4.8 g (87% of theory) of 2-(o-chlorobenzylsulfonyl)-5-trifluoromethyl-1,3,4-thiadiazole of melting point 103° C were obtained.

EXAMPLE 13 (PROCESS VARIANT (C))

(a) Preparation of the sulfochloride

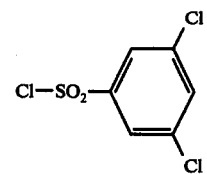

40.5 g (0.25 mole) of 3,5-dichloroaniline were dissolved in a mixture of 110 ml of glacial acetic acid and 135 ml of concentrated hydrochloric acid. A solution of 17.7 g (0.256 mole) of sodium nitrite in 35 ml of water was metered in under the surface of the reaction solution, while stirring at 0° to 5° C, in such a way that no nitrous gases were evolved. At the same time, a saturated solution of sulfur dioxide in 140 ml of glacial acetic acid was prepared and introduced, together with 4 g of copper(I) chloride into a 2 liter vessel. The diazotized solution was introduced in portions (foaming occurred) and when the evolution of nitrogen had subsided, the mixture was diluted with 500 ml of ice water. It was then extracted twice with methylene chloride, the extract was filtered, dried over sodium sulfate and concentrated, and the sulfochloride was distilled in vacuo. 49.2 g (80% of theory) of 3,5-dichlorobenzenesulfochloride of boiling point 83°–84° C/0.1 mm Hg were obtained.

The compounds in the table which follows could be prepared analogously to Examples 8 to 14:

(b)

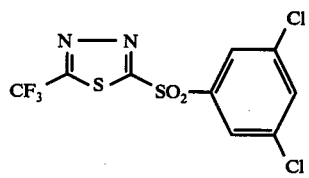
(6)

A solution of 75.6 g (0.6 mole) of analytically pure sodium sulfite in 300 ml of water was pre-warmed to 60°–70° C in a beaker. 122.8 g (0.5 mole) of 3,5-dichlorobenzenesulfochloride, and a solution of 40 g (1 mole) of sodium hydroxide in 200 ml of water were synchronously added dropwise from two dropping funnels in such a way that the pH value (measured with an electrode in the reaction solution) was always between 7 and 9; during the addition the mixture was stirred magnetically. The saline solution of the 3,5-dichlorobenzenesulfinate (about 600 ml) was then diluted with 1.8 liters of dimethylformamide and after adding 116.5 g (0.5 mole) of 2-bromo-5-trifluoromethyl-1,3,4-thiadiazole the whole was stirred for 15 hours at 50° C. The sulfone was precipitated completely by adding ice water and was recrystallized from ethanol. 121 g (70% of theory) of 2-(3′,5′-dichlorophenylsulfonyl)-5-trifluoromethyl-1,3,4-thiadiazole of melting point 123° C were obtained.

Table 8

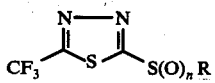

| Compound No. | R | n | Preferred process variant | Melting point/ boiling point (° C) |
|---|---|---|---|---|
| 7 | (pyrazinyl) | 0 | a | 102 |
| 8 | (pyridine N-oxide) | 0 | a | 92 |
| 9 | (pyridyl) | 0 | a | 49–50 |
| 10 | (imidazole-C₆H₅, C₆H₅) | 0 | a | 139 |
| 11 | (thiadiazole-NHCH₃) | 0 | a | 133 |
| 12 | (thiadiazole-N(CH₃)C(O)NHCH₃) | 0 | a | 190 |
| 13 | (benzimidazole-Cl) | 0 | a | 137 |
| 14 | (benzimidazole-OC₂H₅) | 0 | a | 135 |
| 15 | (benzothiazole) | 0 | a | 91 |
| 16 | (benzimidazole) | 0 | a | 188 |
| 17 | (tetrazole-CH₃) | 0 | a | 88 |
| 18 | (thiazoline-N-C₆H₅, =S) | 0 | a | 135 |
| 19 | (thiadiazole-NH₂) | 0 | a | 210 |
| 20 | (dihydrothiazole) | 0 | a | 92 |
| 21 | (thiadiazole-N=CH–N(CH₃)₂) | 0 | a | 140 |
| 22 | (thiazole) | 0 | a | 107 |
| 23 | (imidazole-CH₃) | 0 | a | 119–23 |
| 24 | (thiadiazole-SCH₃) | 0 | a | 110 |
| 25 | (thiadiazole-SO₂CH₃) | 0 | a | 107 |
| 26 | (tetrahydropyrimidine-CH₃) | 0 | a | 147 |
| 27 | —CH₂COOH | 0 | a | 115 |
| 28 | (thiazoline-CH₃, CH₃) | 0 | a | 68 |

Table 8-continued

Structure: 5-CF₃-1,3,4-thiadiazol-2-yl-S(O)ₙR

| Compound No. | R | n | Preferred process variant | Melting point/ boiling point (° C) |
|---|---|---|---|---|
| 29 | 4,5-dihydro-2-methyl-1,3-thiazin-2-yl (N=C(CH₃)–S–CH₂CH₂CH₂–) | 0 | d | 52 |
| 30 | 2,6-dimethoxy-3-methylphenyl | 0 | d | 152 |
| 31 | 2,4-dichlorophenyl | 0 | a | 128 (0.2 mm) |
| 32 | 3-(trifluoromethyl)phenyl | 0 | a | 100–12 (0.4 mm) |
| 33 | 4-chloro-3-(trifluoromethyl)phenyl | 0 | a | 56 |
| 34 | 2-naphthyl | 0 | a | 116 |
| 35 | 2-carboxyphenyl (HOOC-C₆H₄-) | 0 | a | 126 |
| 36 | 2,4-dinitrophenyl | 0 | b | 151 |
| 37 | —CS—N(piperazinyl)—CH₂CH₂OH | 0 | a | 127 |
| 38 | —CS—N(CH₃)₂ | 0 | a | 74–75 |
| 39 | —CS—morpholino | 0 | a | 140 |
| 40 | —CS—piperidino | 0 | a | 68 |
| 41 | 5-methyl-2-(trifluoromethyl)-1,3,4-thiadiazol-yl | 0 | a,b | 92 |
| 42 | 2-methyl-5-nitrothiazol-4-yl | 0 | b | 83 |
| 43 | 4-methyl-2-methylthiazolyl | 0 | b | 113 |
| 44 | —CH₂CH₂C₄F₉ | 0 | b | 40 |
| 45 | 1,2-dimethyl-5-nitro-imidazol-4-yl (NO₂) | 0 | b | 120 |
| 46 | 2-chlorobenzyl (—CH₂—C₆H₄Cl) | 0 | b | 36–37 |
| 47 | 2-methyl-4-isopropyl-1,3,4-thiadiazol-yl | 0 | b | 85 |
| 48 | 3,4-dichlorobenzyl | 0 | b | 135–50 (0.2 mm) |
| 49 | 2,6-dichlorobenzyl | 0 | b | 65 |
| 50 | —CH(C₆H₅)₂ | 0 | b | 75 |
| 51 | —CH₂—CO—C₆H₃(Cl)(Cl) (3,4-dichlorobenzoyl-methyl) | 0 | b | 90 |
| 52 | —CN | 0 | a | 38 |
| 53 | 2,4-dichlorophenyl | 1 | a | 113 |
| 54 | 3,4-dichlorophenyl | 1 | a | 86 |
| 55 | 3,4-dichlorophenyl | 2 | c | 99–100 |
| 56 | 2,4,5-trichlorophenyl | 2 | c | 110 |
| 57 | 4-chlorophenyl | 2 | a,c | 106 |
| 58 | 2,4-dichlorophenyl | 2 | c | 78 |

Table 8-continued

Structure: $CF_3$-[1,3,4-thiadiazole]-$S(O)_n R$

| Compound No. | R | n | Preferred process variant | Melting point/ boiling point (° C) |
|---|---|---|---|---|
| 59 | 2,6-dimethoxyphenyl (CH$_3$O, CH$_3$O) | 2 | a | 136 |
| 60 | 3-trifluoromethylphenyl (CF$_3$) | 2 | c | 83 |
| 61 | naphthyl | 2 | a,c | 73 |
| 62 | 2-hydroxy-benzoic acid (COOH, OH) | 2 | c | 185 (× ½ DMF) |
| 63 | 2-nitrophenyl (NO$_2$) | 2 | c | 113 |
| 64 | tetrahydronaphthyl | 2 | c | 77 |
| 65 | benzoic acid (COOH) | 2 | c | 213 |
| 66 | 2-ethoxyphenyl (C$_2$H$_5$O) | 2 | a | 73 |
| 67 | methyl-nitrophenyl (CH$_3$, NO$_2$) | 2 | c | 130 |
| 68 | acetylphenyl (COCH$_3$) | 2 | c | 65 |
| 69 | chloro-trifluoromethylphenyl (Cl, CF$_3$) | 2 | c | 99 |
| 70 | dichlorophenyl (Cl, Cl) | 2 | c | 100 |
| 71 | propenyl-phenyl | 2 | c | 117 |
| 72 | nitrophenyl (NO$_2$) | 2 | c | 100 |
| 73 | SCF$_3$-phenyl | 2 | c | 74 |
| 74 | phenyl-O-C(F)(F)-O-C(F)(F) (benzodioxole-type) | 2 | c | 120 |
| 75 | cyanophenyl (CN) | 2 | c | 93 |
| 76 | dicyanophenyl (CN, CN) | 2 | c | 125 |
| 77 | nitronaphthyl (NO$_2$) | 2 | c | 174 |
| 78 | —CH$_2$CH$_2$C$_4$F$_9$ | 2 | a | 97 |
| 79 | —CH$_2$-(2,4-dichlorophenyl) | 2 | a | 131 |
| 80 | —CH$_2$-(2,3-dichlorophenyl) | 2 | a | 142 |
| 81 | quinolinyl | 2 | c | 148 |
| 82 | —CH$_2$Cl | 2 | c | 67 |

It will be appreciated that the instant specification and examples are set forth by way of illustration and not limitation, and that various modifications and changes may be made without departing from the spirit and scope of the present invention.

What is claimed is:

1. A 2-substituted 5-trifluoromethyl-1,3,4-thiadiazole of the formula

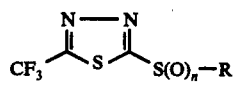

in which
R is phenylalkenyl; phenyl monosubstituted in the o- or m- position, polysubstituted phenyl, or substituted phenylalkenyl, the substituents being selected from alkyl with 1 to 4 carbon atoms, halogenoalkyl, halogenoalkylthio or halogenoalkylsulfonyl each with 1 or 2 carbon atoms and 2-5 halogen atoms, alkoxy, alkylcarbonyl or alkoxycarbonyl each with 1 to 4 carbon atoms in the alkyl moiety, hydroxyl, carboxyl, cyano and thiocyano or naphthyl; 5-membered or 6-membered heterocyclic radical with 1 to 4 hetero-atoms elected from N and S atoms; optionally substituted benzimidiazolyl or benzthiazolyl; optionally substituted naphthyl; quinolyl; cyano or one of the groups

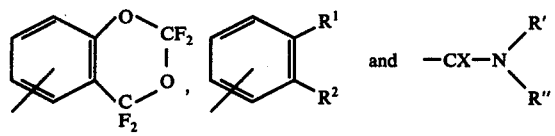

wherein
R¹ and R² conjointly are a trimethylene, tetramethylene or pentamethylene group,
X is oxygen or sulfur,
R' and R" each independently is alkyl or, together with the nitrogen atom and optionally further hetero-atoms selected from O and N atoms, form an optionally substituted 6-membered or 7-membered ring, and
n is 0, 1 or 1.

2. A compound according to claim 1, in which R is phenyl monosubstituted in the o- or m- position, polysubstituted phenyl,

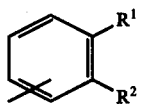

wherein R¹ and R² conjointly are a trimethylene, tetramethylene or pentamethylene group, and phenylalkenyl with 2 to 4 carbon atoms in the alkenyl moiety.

3. A compound according to claim 2, in which R is phenyl monosubstituted in the o- or m- position, polysubstituted phenyl, or

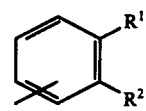

wherein R¹ and R² conjointly are a trimethylene, tetramethylene or pentamethylene group.

4. The compound according to claim 1 wherein such compound is 2-(2'-styrylsulfonyl)-5-trifluoromethyl-1,3,4-thiadiazole of the formula

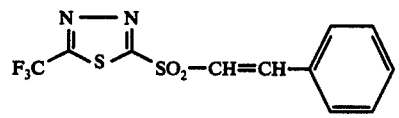

5. The compound according to claim 1 wherein such compound is 2-(3'-chlorophenylsulfonyl)-5-trifluoromethyl-1,3,4-thiadiazole of the formula

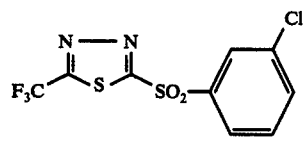

6. The compound according to claim 1 wherein such compound is 2-(3',5'-dimethylphenylsulfonyl)-5-trifluoromethyl-1,3,4-thiadiazole of the formula

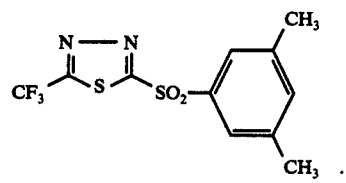

7. The compound according to claim 1 wherein such compound is 2-(3',4'-dichlorophenylsulfonyl)-5-trifluoromethyl-1,3,4-thiadiazole of the formula

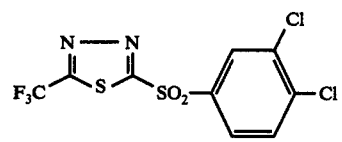

8. The compound according to claim 1 wherein such compound is 2-β-naphthylsulfonyl-5-trifluoromethyl-1,3,4-thiadiazole of the formula

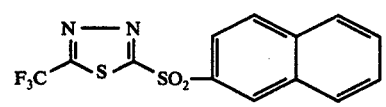

* * * * *

UNITED STATES PATENT AND TRADEMARK OFFICE
CERTIFICATE OF CORRECTION

PATENT NO. : 4,097,669
DATED : June 27, 1978
INVENTOR(S) : Josef Helmut Reisdorff et al It is certified that error appears in the above-identified patent and that said Letters Patent are hereby corrected as shown below:

Col. 33, line 43, Claim 1 - cancel "or 1" and substitute -- or 2 --.

Signed and Sealed this

Twenty-second Day of May 1979

[SEAL]

Attest:

RUTH C. MASON
Attesting Officer

DONALD W. BANNER
Commissioner of Patents and Trademarks